United States Patent [19]

Stewart

[11] Patent Number: 4,903,832

[45] Date of Patent: Feb. 27, 1990

[54] METHOD AND APPARATUS FOR CLEANLY STORING AND DISPOSING OF DISCARDED ARTICLES

[75] Inventor: Gene L. Stewart, San Diego, Calif.

[73] Assignee: Winfield Corporation, San Diego, Calif.

[21] Appl. No.: 299,732

[22] Filed: Jan. 19, 1989

[51] Int. Cl.$^4$ .............................................. B61D 83/10
[52] U.S. Cl. ...................................... 206/366; 220/1 T
[58] Field of Search ............... 206/370, 438, 363, 366, 206/515; 220/1 T, 345, 346

[56] References Cited

U.S. PATENT DOCUMENTS

| | | | |
|---|---|---|---|
| 2,483,304 | 9/1949 | Vogel | 220/35 |
| 4,403,712 | 9/1983 | Wiesinger | 220/339 |
| 4,545,783 | 10/1985 | Vaughan | 604/259 |
| 4,662,516 | 5/1987 | Baker et al. | 206/366 |
| 4,715,498 | 12/1987 | Hanifl | 206/366 |
| 4,802,579 | 2/1989 | Hall et al. | 206/366 |
| 4,809,850 | 3/1989 | Lable | 206/366 |
| 4,828,107 | 5/1989 | Spencer | 206/366 |

*Primary Examiner*—Joseph Man-Fu Moy
*Attorney, Agent, or Firm*—Nydegger & Harshman

[57] ABSTRACT

A system for cleanly storing and disposing of discarded and potentially contaminated articles comprises a disposable receptacle of specialized design and a selectively operable mount for securing the receptacle to a support while in use. The receptacle prior to assembly and deployment on the mount is a unitary nestable sequence of interconnected panels including a rear panel having a back wall, two side walls and a floor extending between the side walls at an acute angle to the back wall to form an open-topped reservoir for trapping fluid from discarded articles. Pivotably mounted to the floor of the rear panel is a face panel which folds into an opposing relationship with the back wall of the rear panel and, by mating with the edges of the side walls, forms above the reservoir an enclosure accessible through an opening formed between the top of the face panel and the top of the back wall. A lid is pivotably attached by an integral hinge to the top of the back wall and biased into closed position occluding the opening to enclosure. Optionally, a guard plate is provided projecting from the lid toward the opening, so that the guard plate at least partially closes the opening when the lid is pivoted out of its closed position. Preferably, all interconnected elements of the nestable sequence of panels are pivotably attached one to another using integral hinges.

40 Claims, 4 Drawing Sheets

METHOD AND APPARATUS FOR CLEANLY STORING AND DISPOSING OF DISCARDED ARTICLES

BACKGROUND OF THE INVENTION

1. Field of the Invention

This invention relates to systems for cleanly storing and disposing of discarded articles which require isolation due to their inherent or acquired dangerousness. More particularly, the present invention relates to a disposable receptacle for medical waste potentially contaminated by the agent of a communicable disease, such as the vector of acquired immune deficiency syndrome (AIDS).

2. Background Art

In the recent past, much attention has been given to controlling the spread of disease through the indiscriminate disposal of contaminated articles, waste, and bodily substances. For most purposes, in a hospital environment, reusable trash receptacles have been deemed adequate for the temporary storage of discarded swabs, bandages, hypodermic needles, and hygiene articles with which the sick have been treated. Nevertheless, such reusable receptacles afford opportunity for disease to be transmitted to medical practitioners or other patients. For example, whenever the receptacles require emptying, contaminants may be disbursed into the environment. Furthermore, the reusable receptacles eventually become contaminated articles themselves. Thus, the desirability of disposing of such containers for potentially contaminated articles has been known.

Even within the context of disposable containers, however, the particular design of a receptacle can significantly contribute to its effectiveness in blocking the spread of disease. Specifically, disposable receptacles that lack lids are open invitations to the spread of any contaminant, and receptacles which can be overturned or from which discarded items can be withdrawn are not secure places in which to discard medical waste.

Typically waste receptacles require a substantial amount of space in which to store discarded articles. This volume requirement associated with waste receptacles has presented problems where the receptacles must be both disposable and secure. Disposability suggests that a large number of the receptacles will be consumed in a given period of time, and accordingly that an adequate number of units to supply needs for a reasonable time will require substantial storage space. In some instances, appropriate designs can permit the nesting of such receptacles to minimize storage space. The need for lids and other types of security structures on receptacles have, however, rendered nesting very difficult if not impossible.

SUMMARY OF THE INVENTION

One object of the present invention is to provide a disposable receptacle capable of securely storing discarded articles and preventing spillage of fluid, if any, carried by those articles.

Yet another object of the present invention is to provide a receptacle which prevents the splashing of fluid from the receptacle when discarded articles are placed into the receptacle.

Yet another object of the present invention is to provide a disposable receptacle which precludes the removal of discarded articles from the receptacle.

An added object of the present invention is to provide a disposable receptacle which is unitary in its construction, to thereby minimizing its cost of manufacture and its simplicity of use.

It is a further object that such a unitary, disposable receptacle be of a design which permits nesting of empty receptacles prior to their assembly and actual use.

A related object of the present invention is to provide means for securely holding the receptacle during use to prevent access or inadvertent upset.

Still another object of the present invention is to provide a signal which will indicate when the receptacle is full of discarded articles and should be disposed.

Further in this regard, it is desirable that the receptacle of the system envisioned be easily removal from the mounting mechanism of the system by authorized persons.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a unitary, disposable, secure receptacle for discarded articles is provided in one embodiment of the invention with a rear panel and a lid and face panel which are pivotably attached to the rear panel. Preferably, the pivotal attachments are accomplished by integral hinges. The rear panel has a back wall, two side walls projecting from the back wall, and a floor extending from the back wall at an acute angle thereto. The floor interconnects the two side walls to form a reservoir with the back and side walls for trapping fluid from discarded articles. The reservoir is open at the top, having an entry thereto bounded by the back wall, the side walls, and an edge of the floor extending between the side walls apart from the back wall.

The face panel is pivotably attached to the edge of the floor described above and is configured to be engagable with the side walls when pivoted into an opposing relationship with the back wall of the rear panel. In this position, the face panel closes a first portion of the entry to the fluid-trapping reservoir. Cooperating fastening means on the face panel and the side walls retain the face panel and the back wall in their opposing relationship.

In one embodiment of the present invention, the face panel and the back and side walls of the rear panel form an enclosure above the entry to the reservoir for discarded articles. This enclosure is accessible through an opening formed between the top of the face panel and the top of the back wall. The lid is pivotably attached to the top of the back wall to block a second portion of the entry to the reservoir, which second portion comprises substantially all of the entry distinct from the first portion thereof closed by the face panel. The closed position of the lid thus covers the opening to the enclosure for discarded articles. Additionally, but advantageously, the lid includes a guard plate which projects from the lid at an angle such that the guard plate at least partially closes the opening to the enclosure when the lid is pivoted out of its closed position. When the lid is in its closed position, the guard plate is housed in the interior of the enclosure.

The rear panel, face panel, and lid, form a unitary sequence of interconnected panels. When the face panel is not in its opposing relationship with the back wall of the rear panel, this sequence of interconnected panels can economically be laid out and nested with other such sequences of panels to economize shipping and storage space prior to their use. The disposable receptacle in this unfolded condition is easily converted into a functioning disposable receptacle by pivoting the face panel against the rear panel.

In another aspect of the present invention, mounting means are provided for securing the receptacle to a support, such as a wall. Additionally, the mounting means also includes a spring loaded flap for biasing the lid of the receptacle into its closed position. By way of example, the mounting means includes mounting fingers on the exterior of the back wall of the receptacle which is engageable with a mount that is securable to the support.

As disclosed herein, the mount includes a base plate that is securable to the support, and a lid-biasing flap that is resiliently mounted at the top of the base plate for urging the lid of the receptacle into its closed position when the receptacle is secured on the mount. A locking plate slidably mounted to the base plate is capable of movement between a receiving position and a retaining position, but is biased into the latter. In the receiving position, the mounting finger on the receptacle is free of the locking plate, while in the retaining position the mounting fingers are captured thereby to secure the receptacle to the base plate. Since the locking plate is concealed by the receptacle when the receptacle is secured to the mount, a key is provided which can be inserted between the receptacle and the base plate from either side to move the locking plate out of its retaining position and into the receiving position in order to free the mounting finger and the receptacle from the mount. Thereafter, disposal of the receptacle may be effected.

Optionally, an indicator can be incorporated which is engageable with the lid to provide a time delayed visual signal whenever the lid remains open for a preselected time interval. Importantly, this signal is used to indicate when the receptacle is full of discarded articles and should be disposed. Specifically, any inability of the integral guard plate to return to its lid-closed position, such as is caused when the receptacle is full of discarded articles, will generate the signal.

The present invention also contemplates a method for cleanly storing and disposing of discarded articles. Furthermore, it is anticipated that a disposable receptacle designed specifically for use in the medical field, will also have application in other areas in which contamination from discarded articles is to be minimized. For example, the safe disposal of laboratory and factory wastes is contemplated by the present invention in the embodiment shown and described hereafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DESCRIPTION OF THE PREFERRED EMBODIMENT

Figure 1:
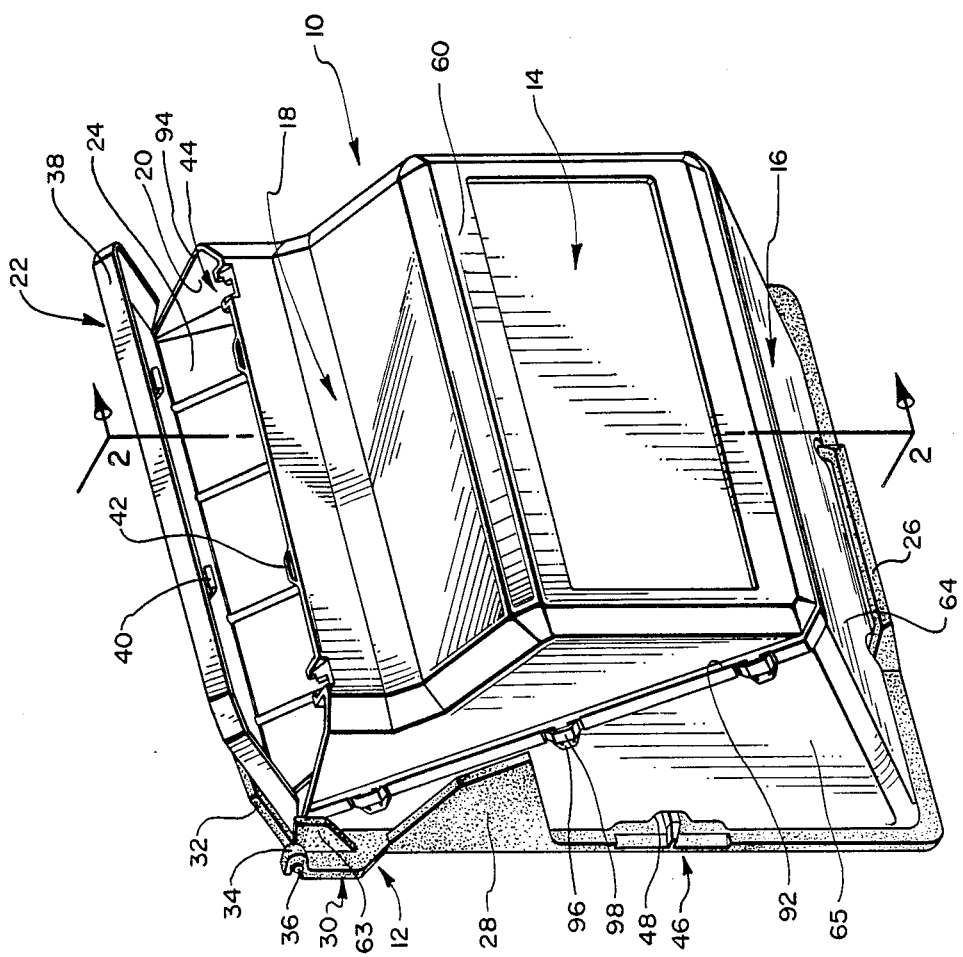
FIG. 1 is a perspective view of a disposable receptacle for discarded articles attached to a mount for securing the receptacle to a support.

Shown in FIG. 1 is a disposable receptacle 10 embodying teachings of the present invention. Receptacle 10 is held against a planar vertical support, such as a wall or post (not shown) by a mount 12 which can be secured to the support. The exterior view of receptacle 10 provided in FIG. 1 discloses that receptacle 10 includes a relatively voluminous body portion 14 between a tapering reservoir portion 16 therebelow and a narrow neck portion 18 terminating in an opening 20 thereabove. Opening 20 is occludable by a lid 22 pivotably mounted to receptacle 10 at the side of opening 20 adjacent to mount 12. Lid 22 is shown in FIG. 1 disposed in an orientation intermediate the closed and open positions thereof. In the closed position, lid 22 blocks opening 20. In the open position, lid 22 will have a vertical orientation substantially parallel to the plane of mount 12. In that open position, a guard plate 24 projecting from lid 22 proximate to mount 12 substantially blocks opening 20 toward an end to be described subsequently.

Mount 12 includes a plurality of components which are not visible in FIG. 1. Nevertheless, FIG. 1 does reveal that mount 12 includes a projecting support 26 at the bottom of reservoir portion 16 of receptacle 10 to assist in upholding receptacle 10 on mount 12. To either side of receptacle 10 mount 12 includes projecting alignment ears 28 for orienting receptacle 10 on mount 12, as well as a laterally extending hinge plate portion 30 by means of which a lid-biasing flap 32 is resiliently mounted at the top of mount 12.

Lid-biasing flap 32 bears against the top of lid 22 and urges it into a closed position when receptacle 10 is secured to mount 12. A semicircular sleeve 34 on hinge plate portion 30 cooperates with a shaft 36 rigidly secured to lid-biasing flap 32 to enable pivotal movement of lid-biasing flap 32. When lid 22 is lifted out of its closed position, lid-biasing flap 32 is pivoted upwardly. A skirt 38 also mounted on hinge plate portion 30 adjacent to and laterally interior of sleeve 34 blocks downward pressure from lid-biasing flap 32 onto lid 22 beyond a predetermined lower threshold to prevent tight closure of lid 22. At the predetermined lower threshold of lid-biasing flap 32 a skirt 38 at the periphery of lid 22 encloses the perimeter of opening 20, without engaging cooperating lid lock structures 40 and 42 on lid 22 and neck portion 18, respectively. It is the purpose of lid lock structures 40, 42 to effect the permanent closure of receptacle 10 in preparation for the removal of receptacle 10 and its contents from mount 12 prior to disposal.

Optionally, to facilitate the disposal of hypodermic needles, a hypodermic needle hub gripper 44 is located interior to opening 20. With the hub of a hypodermic needle inserted into an appropriately sized slot of hypodermic needle hub gripper 44, counterclockwise rotation of the hypodermic syringe to which that hub and needle are attached will result in their removal and fall into the interior of receptacle 10 without further handling.

The interaction of the components of receptacle 10 and mount 12 described thus far will be better appreciated through a description of the balance of the figures accompanying this disclosure. Nevertheless, prior to passing to FIG. 2, it should be noted that mount 12 is provided at a position behind reservoir portion 16 of receptacle 10 with a raised key guide 46 utilized with an appropriate keying device not shown in FIG. 1 to effect the selective removal of receptacle 10 from mount 12. Key guide 46 is housed within a key recess 48 in the periphery of the rest portion of receptacle 10. Together key guide 46 and key recess 48 direct the keying mechanism between mount 12 and receptacle 10 when the release of receptacle 10 is desired.

Figure 2:
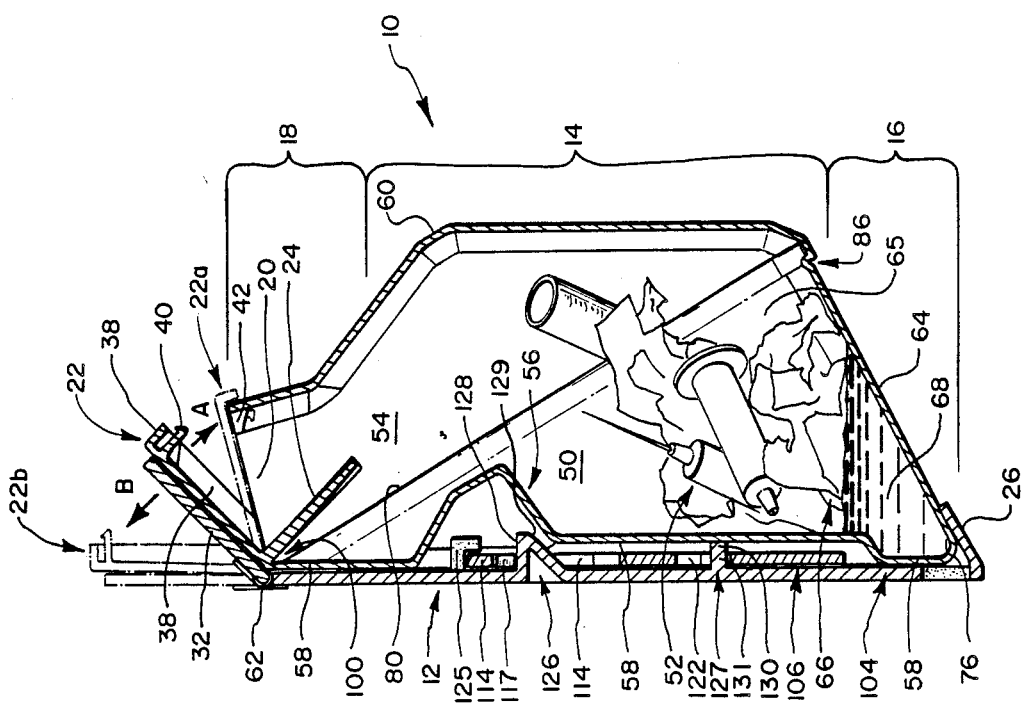
FIG. 2 is a cross-section of the receptacle and mount shown in FIG. 1 taken along section line 2—2 shown in FIG. 1.

The operation of receptacle 10 in receiving and retaining discarded articles is most clearly understood by reference to FIG. 2. There, structural elements already described in relation to FIG. 1 are designated by identical reference characters. Body portion 14 of receptacle 10 surrounds enclosure 50 which receives and retains discarded articles 52 such as swabs, bandages, hypodermic needles, and hygiene materials. These discarded articles 52 fall into enclosure 50 through a passageway 54 extending thereabove between opening 20 and enclosure 50.

To preclude the removal from receptacle 10 of discarded articles 52 placed therein, passageway 54 is intentionally designed to be a non-linear, tortuous passageway. This is accomplished by routing passageway 54 about the obstruction of a laterally extending indent 56 in the back wall 58 of receptacle 10 and correspondingly narrowing front wall 60 from protruding body portion 14 to narrow neck portion 18 at and above indent 56. The opening of indent 56 at either side of receptacle 10 is obscured in FIG. 1 by alignment ears 28.

The cross-sectional view afforded in FIG. 2 discloses structure associated with mount 12 that is used to attach receptacle 10 thereto. The operation of such structure will be described in detail in relation to the eventual discussion of FIG. 4. At that point the views provided in FIG. 2 will prove helpful to a full understanding. For the present, however, other aspects of receptacle 10 will be addressed.

In FIG. 2, lid 22 is shown pivoted into a position intermediate a closed position 22a and an open position 22b, both shown in phantom. Lid-biasing flap 32 under the influence of bias spring 62 bears against the top of lid 22 forcing it in the direction indicated by arrow A into closed position 22a. In that position, guard plate 24 is housed in passageway 54 adjacent to back wall 58 of receptacle 10. On the other hand, in order to deposit a discarded article into receptacle 10, lid 20 is pivoted against the biasing influence of lid-biasing flap 32 in the direction of arrow B into open position 22b. In that position, guard plate 24 at least partially closes opening 22. An article to be discarded is placed on guard plate 24, and lid 22 is released. Lid-biasing flap 32 then promptly pivots lid 22 into closed position 22a, rotating guard plate 24 downwardly toward back wall 58 of receptacle 10 in the process. The discarded articles falls from guard plate 24 through passageway 54 into enclosure 50. As mentioned previously, however, full closure of lid 22 against the edges of opening 20, which would result in the engagement of permanent lid lock structures 40 and 42, does not occur in this process due to stop 63 shown in FIG. 1.

In another aspect of the present invention, floor 64 of receptacle 10 is inclined upwardly at an acute angle to back wall 58 between and interconnecting opposite side walls 66 of receptacle 10. Thusly formed in reservoir portion 16 of receptacle 10 is an open-topped reservoir 66 for trapping fluid 68 either directly or in association with discarded articles 52. Advantageously, the portion of receptacle 10 surrounding reservoir 66 is of a unitary construction, whereby to prevent leakage of fluid 68. So long as receptacle 10 is maintained in its proper orientation through its attachment to mount 12 as shown in FIG. 2, both discarded articles 52 and fluid 68 will be safely isolated from the environment in which receptacle 10 is employed.

The manner in which receptacle 10 is removed from mount 12 ensures that only qualified personnel trained to dispose receptacle 10 without spilling fluid 68 will do so. This is accomplished by requiring a properly fitted keying apparatus to release receptacle 10 from mount 12. The keying apparatus cooperates to do so with key guide 46 and key recess 48 shown in FIG. 1.

In the proper disposal of discarded articles potentially contaminated by victims of AIDS, where bodily fluids play a significant role in communication of the disease, a fluid-trapping reservoir, such as reservoir 66, can be significant. Also of significance is the non-linear nature of passageway 54, which reduces the likelihood of the splashing of fluid 68 and enhances organized stacking of discarded articles 52 deposited in receptacle 10. Caution with regard to fluid 68 is further enhanced by the cooperating action of guard plate 24 and lid 22. Guard plate 24 substantially blocks opening 20 when lid 22 is in the open position 22b thereof, preventing discarded articles from falling into reservoir 66 until lid 22 is being returned under the influence of lid bracing flap 32 to the closed position 22a thereof. By then, while the discarded article originally placed on guard plate 24 is falling into receptacle 10, skirt 38 on lid 22 has effected closure of opening 20.

Figure 3:
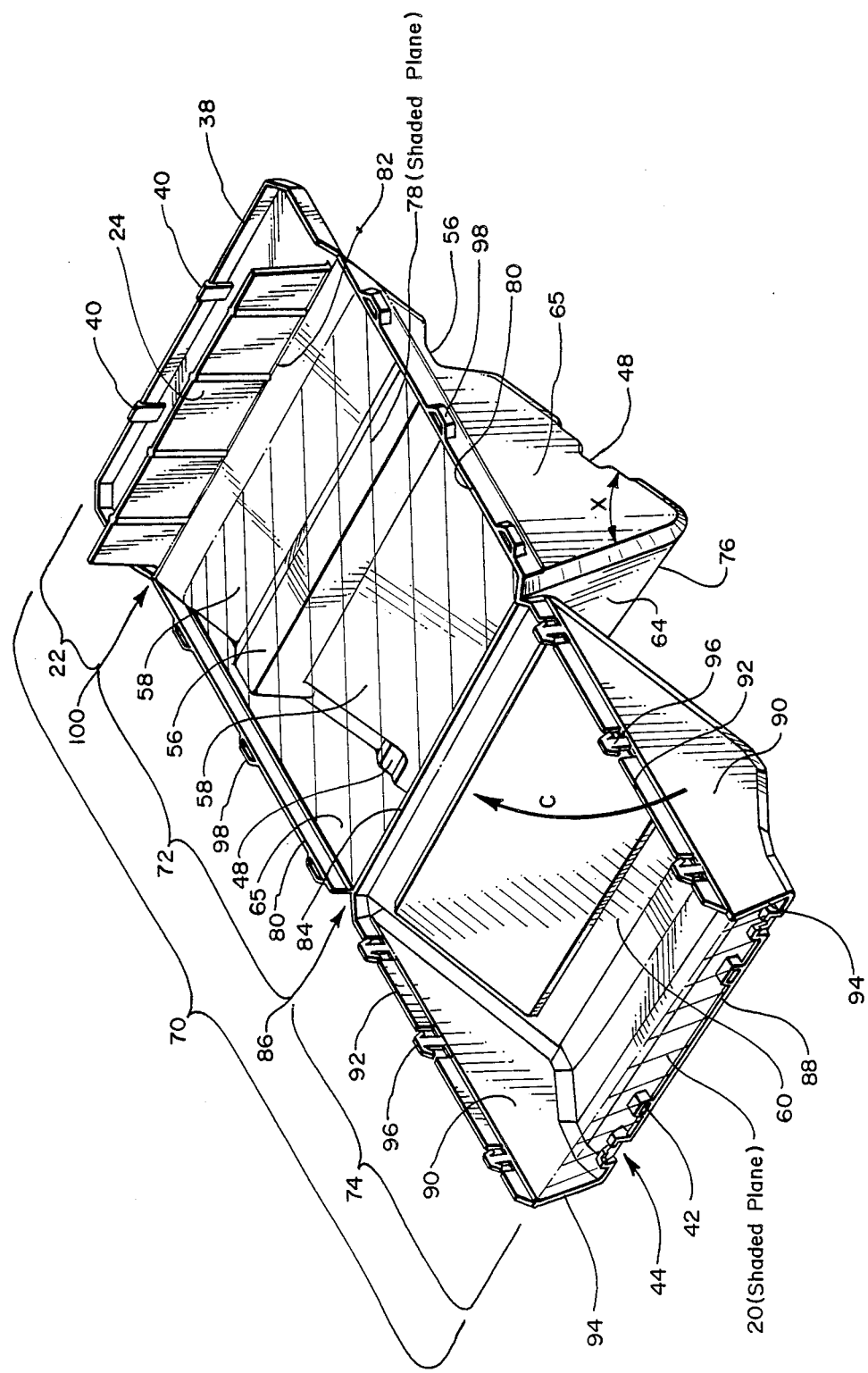
FIG. 3 is a perspective view of the receptacle of FIGS. 1 and 2 shown in its unfolded, nestable condition.

Another aspect of the disposable receptacle of the present invention is graphically illustrated in FIG. 3. There, receptacle 10 of FIGS. 1 and 2 is revealed in its disassembled state to comprise a unitary, nestable sequence 70 of interconnected panels. Specifically, nestable sequence 70 comprises a rear panel 72 and a face panel 74 and lid 22 connected thereto. Rear panel 72 includes back wall 58 for attachment to a mount, such as mount 12, two side walls 65 projecting from back wall 58 in a direction opposite from that at which such a mount would be located, and floor 64 extending from back wall 58 in that same direction at an acute angle X. Together these components of rear panel 72 which meet at the vertex 76 of angle X form reservoir 66, which in one analysis of the present invention can be seen to have an entry 78 shown in FIG. 3 as a shaded plane bounded by the edges of the four sides of reservoir 66 remote from vertex 76 of angle X. The boundaries of entry 78 thus comprise free edges 80 of side walls 65, top edge 82 of back wall 58, and a forward edge 84 of floor 64 extending between side walls 65.

Face panel 74 is pivotably attached to rear panel 72, preferably by an integral hinge 86, at forward edge 84 of floor 64. Face panel 74 includes front wall 60 having a top edge 88 remote from integral hinge 86 and projecting side walls 90 each having an edge 92 opposite front wall 60 and a top edge 94 remote from integral hinge 86. Face panel 74 may be pivoted in the direction indicated by arrow C about integral hinge 86 toward rear panel 72 and into an opposing relationship with back wall 58 thereof. Edges 92 of side walls 90 of face panel 74 mate with edges 80 of side walls 65 of rear panel 72, and in this manner rear panel 72 and face panel 74 form enclosure 50 above reservoir 66, as shown in FIG. 2. Under one analysis of the present invention face panel 74 will be appreciated as closing a first portion of entry 78 to reservoir 66, while leaving open a second portion of entry 78 accessible through opening 20 shown in FIG. 3 as a shaded plane.

Cooperating fastening means, typified by fastening structures 96, 98 at opposed locations on edges 92, 80, respectively, engage each other when rear panel 72 is in its opposing relationship with back wall 58. This permanently secures nestable sequence 70 into the assembled form of receptacle 10 shown in FIGS. 1 and 2.

Prior to such an assembly, however, sequence 70 is nestable with other identically configured and identically attached panels. This feature of the present invention permits pre-use shipment and storage of receptacles, which is highly efficient as to space consumption. Once nestable sequence 70 is folded into receptacle 10, however, a voluminous enclosure 50 results for storing discarded articles. Below enclosure 50 is an open-topped reservoir 66 for trapping fluid therefrom. This transformation of generally planar nestable sequence 70 into an enclosed space secure for the storage and disposal of potentially contaminated articles contributes to substantial economies in terms of manufacture, shipping, ease of use, and durability.

Nestable sequence 70 comprises one additional panel, namely lid 22 with guard plate 24 projecting therefrom, which has been described above in relation to FIGS. 1 and 2. Lid 22 is attached to rear panel 72 at top edge 82 of back wall 58, preferably by an integral hinge 100. Integral hinge 100 may be formed so as to be self-closing, thereby obviating somewhat the necessity for external biasing means, such as lid-biasing flap 32. In this manner, lid 22 can be pivoted in and out of the closed position 22a thereof in order to block the second portion of entry 78 to reservoir 66 that equates with opening 20.

In a further aspect of the present invention in a system for cleaning, storing, and disposing of discarded articles, in cooperation with a disposable receptacle, such as receptacle 10, mounting means are provided for securing the receptacle to a support and, optionally, for biasing the lid of that receptacle into its closed position. As shown by way of example and not limitation in FIG. 4, such a mounting means suitable for the purposes of the present invention comprises a support-securable, plural-component mount 12 and cooperating means associated with rear panel 72 of receptacle 10 for holding receptacle 10 onto mount 12. In the embodiment illustrated in FIG. 4, such a cooperating means comprises a pair of mounting fingers 102 on the exterior of back wall 58. Mounting fingers 102 are housed within indent 56 so as to engage cooperating elements of mount 12 in a manner to be described.

Mount 12 comprises a base plate 104, a locking plate 106, and lid-biasing flap 32. Base plate 104 is securable by any known means, such as screws (not shown) and eyelets 108 to a support (also not shown). Lid-biasing flap 32 is resiliently mounted at the top 110 of base plate 104 using spring 62.

The attachment of receptacle 10 to base plate 104 in a manner which permits the selective removal of receptacle 10 for discarding same is effected by locking plate 106. Once assembled to base plate 104, locking plate 106 is slidable between a receiving position 106a, shown in FIG. 4 in heavy phantom, and a retaining position 106b, shown in FIG. 4 in light phantom. Locking plate 106 is biased into the closed position 106b thereof. The movement between receiving position 106a and retaining position 106b is indicated by arrows D.

To emplace locking plate 106 against base plate 104, some features of each must be described. Locking plate 106 includes a pair of upstanding mounting hooks 112 at either side of the top thereof. These each have an upper beveled edge 113. Therebelow, a central portion of locking plate 106 is formed into a biasing cutout 114 into which form either side project an elongated biasing arm 116 having a rounded end 117. Once locking plate 106 is mounted on base plate 104, biasing arms 116 urge locking plate 106 into retaining position 106b. Below biasing cutout 114 locking plate 106 assumes an hourglass shape due to the formation in opposed side edges of locking plate 106 of keying indents 118. These cooperate with key guide 46 and a suitably formed key 120 when receptacle 10 is mounted on mount 12 covering access to locking plate 106, to overcome the urging of biasing arms 116 and to move locking plate 106 from retaining position 106b into receiving position 106a. In this manner the ability to disengage receptacle 10 from mount 12 is limited to those trusted individuals granted access to a key, such as key 120. Between keying indents 118 is a T-shaped mounting and alignment cutout 122 comprising a horizontal slot 123 and a vertical slot 124.

Correspondingly, on base plate 104 are a pair of upper stops 125, an upstanding biasing footing 126, and an upstanding mounting and alignment pin 127. Upper stops 125 restrain upward movement of locking plate 106 beyond retaining position 106b. The width of biasing footing 126 is greater than the distance between rounded ends 117 of opposing biasing arms 116 on locking plate 106. Biasing footing 126 has a laterally extending bearing surface 128 at the top thereof and an inclined mounting ramp 129 therebelow. Mounting and alignment pin 127 has a broad head 130 shorter than the length of the horizontal slot 123 of mounting and alignment cutout 122 but wider than vertical slot 124 therebelow. Head 130 is upheld above base plate 104 a distance greater than the thickness of locking plate 106 by a stem 131.

To mount locking plate 106, it is placed against base plate 104 so that mounting and alignment pin 127 passes through horizontal slot 123 of mounting and alignment cutout 122. Simultaneously, biasing footing 126 projects into biasing cutout 114 above biasing arms 116. This position of locking plate 106 corresponds roughly to receiving position 106a thereof. Thereafter, while being made to bear against base plate 104, locking plate 106 is advanced upwardly toward upper stops 125 and retaining position 106b.

Stem 131 of mounting and alignment pin 127 travels in vertical slot 124 of mounting and alignment cutout 122, while the rounded ends 117 of biasing arms 116 gradually are forced away from base plate 104, outwardly from the plane of locking plate 106, as they encounter inclined mounting ramp 129 of biasing footing 126. As this process continues, biasing arms 116 advance to the top of mounting ramp 129 and snap over the top of biasing footing 126 and back into the plane of locking plate 106. Thereafter, resilient biasing arms 116 are distorted upwardly in the plane of locking plate 106 out of the positions thereof shown in FIG. 4. Rounded ends 117 thereof bear against bearing surface 128 of biasing footing 126 in the manner shown in cross-section in FIG. 2. As a result of the tendency of biasing arms 116 to return to the positions thereof shown in FIG. 4, locking plate 106 is urged upwardly into retaining position 106b.

The attachment of receptacle 10 to thusly assembled mount 12 occurs as follows. Reservoir portion 16 of receptacle 10, and more specifically vertex 76 of angle X, is set upon support 26 on base plate 104. Cooperating dimples 132 in vertex 76 assist in this alignment. Thereafter, receptacle 10 is pivoted on support 26 toward mount 12 into a position between alignment ears 28. Mounting fingers 102 in indent 56 in back wall 58 of receptacle 10 encounter upper beveled edge 113 on mounting hooks 112. Continued pressure of receptacle 10 toward base plate 104 causes mounting fingers 102 to lever locking plate 106 downwardly out of retaining position 106b as mounting fingers 102, which are with receptacle 10 held stationary, ride over beveled edges 113 to the top of mounting hooks 112. At this point, impedance to the movement of back wall 58 toward base plate 104 ceases, and mounting fingers 102 slide over the hook portion of mounting hooks 112. The effect of biasing arms 116 then promptly returns locking plate 106 to retaining position 106b, and mounting hooks 112 seize mounting fingers 102 to hold receptacle 10 in position on mount 12.

Figure 4:
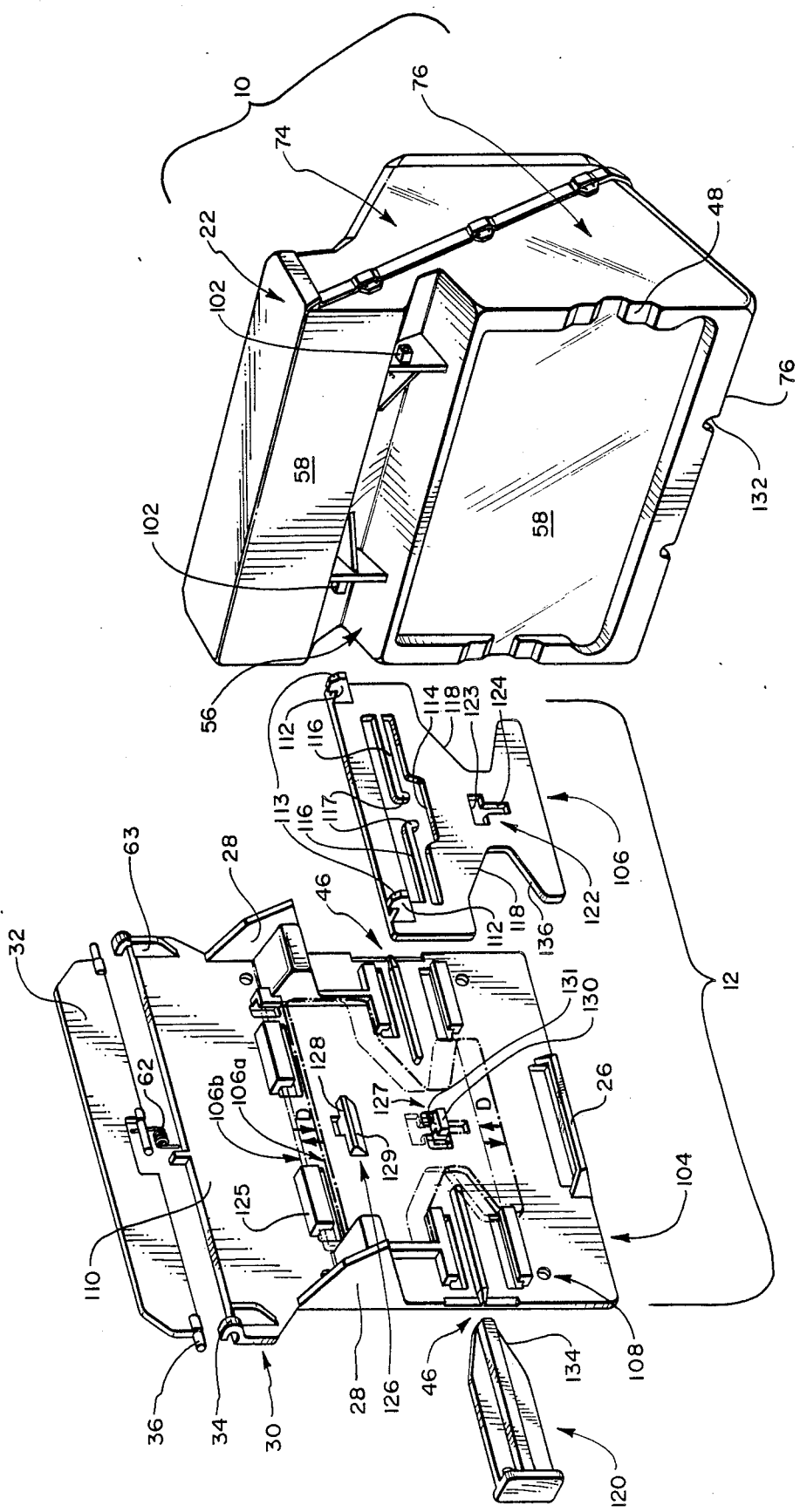
FIG. 4 is an exploded perspective view of the receptacle and the elements of the mount therefor shown in FIG. 1.

The removal of receptacle 10 from its mounted position is effected through the use of key 120, which is inserted between receptacle 10 and base plate 104 to ride on key guide 46. An inclined lower leading edge 134 of key 120 eventually encounters a lower sloping edge 136 of keying indent 118. Continued lateral pressure on key 120 forces locking plate 106 out of retaining position 106b. Key guide 46 holds key 120 stationary vertically, and lower sloping edge 136 of keying indent 118 rides downwardly as seen in FIG. 4 upon lower leading edge 134 of key 120. Once this process has moved locking plate 106 into receiving position 106a, mounting hooks 112 will have been lowered adequately to free mounting fingers 102. Then receptacle 10 may be pivoted on support 26 away from mount 12 and discarded with its contents.

The disclosed mounting system ensures that receptacle 10 will not be overturned and can be secured safely out of reach of curious individuals. Receptacle 10 can only be removed from the support for mount 12 by qualified personnel in possession of key 120. Lid-biasing flap 32 bears against lid 22 to maintain the opening 20 to receptacle 10 in closed position 22a.

Figure 5:
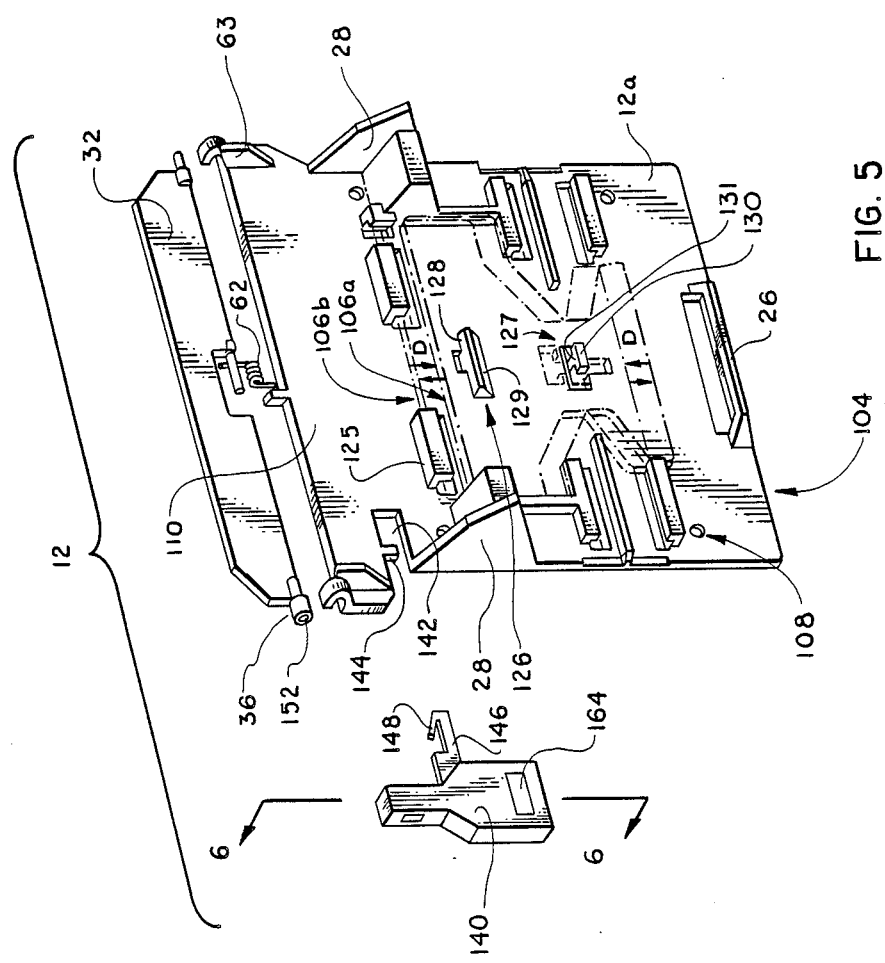
FIG. 5 is a perspective view of the mount of the present invention shown in positional relationship with an indicator for signaling when the receptacle is full.

Referring now to FIG. 5, it will be seen that an indicator 140 can be provided which is engageable with a modified mount 12a. Specifically, mount 12a is formed with a recess 142 and a tang 144 which extends into the recess 142. The indicator 140 is formed with an extension 146 which is engageable with recess 142 to hold indicator 140 in a side-by-side relationship with mount 12a and the receptacle 10 when receptacle 10 is engaged with mount 12a. More specifically, as shown in FIG. 5, extension 146 of indicator 140 is formed with a flexible finger 148 which is depressed by tang 144 as extension 146 is inserted into recess 142. Once extension 146 is fully seated in recess 142, finger 148 is no longer depressed by tang 144. Instead, finger 148 is released to position itself against tang 144 and hold indicator 140 next to mount 12a.

Figure 6:
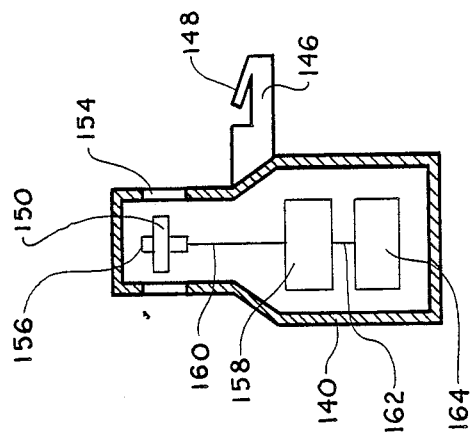
FIG. 6 is a cross-sectional view of the indicator as seen along the line 6—6 in FIG. 5.

While extension 146 engages with recess 142 to hold indicator 140 against mount 12a, shaft 136 of lid-biasing flap 32 operatively engages with activator arm 150 of indicator 140. As shown in FIG. 5, shaft 36 is formed with an indent 152. As shown in FIG. 6, activator arm 150 is mounted for rotation in indicator 140 so as to be engageable with shaft 36 when the shaft 36 is inserted through opening 154 of indicator 140. Although indent 152 is shown in FIG. 5 to be rectangular in shape, this is only exemplary. Indeed, indent 152 can be of any configuration so long as it is compatible with arm 150 for engagement and rotation with activator arm 150. Thus, for a rectangular indent 152, activator arm 150 must also be rectangular.

With specific reference to FIG. 6, it is to be appreciated that activator arm 150 is rotationally mounted on a switch 156 inside indicator 140. As so mounted, activator arm 150 is moveable to change switch 156 between an "on" and an "off" condition in any manner well known in the pertinent art. Further, switch 156 is electrically connected to electronic components 158 via line 160 and components 158 are electrically connected via line 162 to display 164. With this combination, display 164 can be used to provide a visual indication of the position of switch 156. This, in turn, will indicate the relative position of lid-biasing flap 32. Further, electronic components 158 can include a timer (not shown) which delays any indication of a change in the position of switch 156 at display 164 until after the position change has lasted for longer than a preselected time interval. For example, consider switch 156 to be in its "off" position when flap 32 rests against a closed lid 22. When lid 22 is raised in the direction of arrow B, as shown in FIG. 2, flap 32 will be rotated to a point where switch 156 will change to its "on" position. If lid 22 and flap 32 are released within a preselected time interval, for return movement to their closed position, display 164 will not indicate the change in switch 156. On the other hand, if lid 22 and flap 32 do not return to their closed position within the preselected time interval, display 164 will indicate a lid open condition. Importantly, when the build up of discarded articles 52 in enclosure 50 is such that guard plate 24 cannot return to its respective lid 22a closed position, switch 156 will be held in its "on" position and after the preselected time interval, display 164 will be activated. Receptacle 10 should then be removed from mount 12a and discarded.

While FIG. 5 and FIG. 6 show a combination wherein the indicator 140 is positioned on the left side of mount 12a, it is to be appreciated that indicator 140 and mount 12a can be configured to position indicator 140 on the right side of mount 12a. In either case, the engagement of indicator 140 with mount 12a and the operation of indicator 140 will be essentially as discussed above.

By way of example, functionally acceptable embodiments of the inventive receptacle and mounting system have been produced by injection molding using a 500T (3T/in.²) molding machine. The resulting receptacle held a minimum of 500 milliliters of fluid, projected 4.5 inches from a support when attached to the mount therefor, and was adequately nestable in its unfolded condition to permit efficient shipping and storage. The receptacle produced had a minimum capacity of one hundred fifty (150) 3-cc syringes and enjoyed an opening measuring 1⅜ by 8 inches. The device included all features disclosed above and was capable of manufacture at a reasonable cost.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A unitary, disposable, fluid-trapping receptacle for discarded articles, the receptacle comprising:
   (a) a rear panel having a back wall, two side walls projecting from said back wall, and a floor extending from said back wall at an acute angle interconnecting said side walls to form a reservoir for trapping fluid contained in the discarded articles, said reservoir having an entry bounded by said back wall, said side walls, and an edge of said floor extending between said side walls separated from said back wall;
   (b) a face panel pivotably attached to said edge of said floor by an integral hinge, said face panel being engagable with said side walls to close a first portion of said entry and to retain said face panel in an opposing relationship with said back wall; and
   (c) mounting means for securing said receptacle to a support.

2. A disposable receptacle as recited in claim 1, wherein said rear panel with said face panel pivotably attached thereto is nestable with other identically configured and identically attached rear and face panels when said face panel and said back wall are out of said opposing relationship.

3. A disposable receptacle as recited in claim 1, further comprising fastening means on said face panel and said side walls for retaining said face panel and said rear panel in said opposing relationship.

4. A disposable receptacle as recited in claim 1, wherein said mounting means comprises:
   (a) a mount securable to the support; and
   (b) cooperating means associated with said back wall for holding said receptacle on said mount.

5. A disposable receptacle as recited in claim 1, further comprising a lid pivotably attached to said back wall at said entry, said lid having a closed position blocking a second portion of said entry comprising substantially all of said entry distinct from said first portion thereof.

6. A disposable receptacle as recited in claim 5, further comprising a guard plate projecting from said lid toward said second portion of said entry, said guard plate at least partially closing said second portion of said entry when said lid is pivoted out of said closed position thereof.

7. A disposable receptacle as recited in claim 6, further comprising a flap hingedly attached to said mounting means and spring loaded to urge against said lid to bias said lid into said closed position thereof.

8. A disposable receptacle as recited in claim 7, further comprising an indicator operatively connected to said flap to provide a visual signal signifying the position of said lid.

9. A disposable receptacle as recited in claim 5, wherein said lid is pivotably attached to said rear panel by an integral hinge.

10. A disposable receptacle as recited in claim 5, further comprising a hypodermic needle hub gripper located interior said second portion of said entry.

11. A unitary, disposable, fluid-trapping receptacle for discarded articles, the receptacle comprising:
    (a) a rear panel having a back wall, two side walls projecting from said back wall, and a floor extending from said back wall at an acute angle interconnecting said side walls to form a reservoir for trapping fluid contained in the discarded articles, said reservoir having an entry bounded by said back wall, said side walls, and an edge of said floor extending between said side walls separated from said back wall;
    (b) a face panel pivotably attached to said edge of said floor by an integral hinge, said face panel being engagable with said side walls to close a first portion of said entry and to retain said face panel in an opposing relationship with said back wall;
    (c) fastening means on said face panel and said side walls for retaining said face panel and said back wall in said opposing relationship; and
    (d) a lid pivotably attached to said back wall at said entry, said lid having a closed position blocking a second portion of said entry comprising substantially all of said entry distinct from said first portion thereof.

12. A disposable receptacle as recited in claim 11, wherein said rear panel with said face panel and with said lid pivotably attached thereto is nestable with other identically configured and identically attached rear and face panels when said face panel and said back wall are out of said opposing relationship.

13. A disposable receptacle as recited in claim 11, further comprising a guard plate projecting from said lid toward said second portion of said entry, said guard plate at least partially closing said second portion of said entry when said lid is pivoted out of said closed position thereof.

14. A disposable receptacle as recited in claim 11, further comprising a hypodermic needle hub gripper located interior said second portion of said entry.

15. A disposable receptacle as recited in claim 11, further comprising a mounting means for securing said receptacle to a support, said mounting means comprising:
    (a) a mount securable to the support; and
    (b) cooperating means associated with said back wall for holding said receptacle on said mount.

16. A disposable receptacle as recited in claim 11, further comprising a flap hingedly attached to said mounting means and spring loaded to urge against said lid to bias said lid into said closed position thereof.

17. A disposable receptacle as recited in claim 16, further comprising an indicator operatively connected to said flap to provide a visual signal signifying the position of said lid.

18. A disposable receptacle as recited in claim 15, wherein said cooperating means is selectively detachable from said mount.

19. A disposable, fluid-trapping, support-mountable receptacle for discarded articles, the receptacle comprising:
(a) a rear panel having a back wall for mounting to the support, two side walls projecting from said back wall in a direction opposite the support, and a floor interconnecting said side walls and said back wall, said floor being inclined upwardly from said back wall when said receptacle is mounted to the support to form in combination with said back wall and said side walls an open-topped reservoir for trapping fluid from the discarded articles;
(b) a face panel in an opposing relationship with said back wall attached to said side walls and to said floor at a point therebetween to form above said reservoir an enclosure accessible through an opening formed between the top of said face panel and the top of said back wall;
(c) a tortuous passageway between said enclosure and said opening; and
(d) a lid pivotably attached to said top of said back wall, to occlude said opening in a closed position of said lid.

20. A disposable receptacle as recited in claim 19, wherein said rear panel with said face panel and with said lid pivotably attached thereto is nestable with other identically configured and identically attached rear and face panels when said face panel and said back wall are out of said opposing relationship.

21. A disposable receptacle as recited in claim 19, wherein said face panel is attached to said floor of said rear panel by an integral hinge.

22. A disposable receptacle as recited in claim 21, further comprising fastening means on said face panel and said side walls of said rear panel for retaining said face panel and said back wall in said opposing relationship.

23. A disposable receptacle as recited in claim 19, said receptacle further comprising a guard plate projecting from said lid toward said opening proximate said back wall, said guard plate at least partially closing said opening when said lid is pivoted out of said closed position thereof and being housed within said tortuous passageway adjacent said back wall when said lid is in said closed position thereof.

24. A disposable receptacle as recited in claim 19, wherein said lid is attached to said top of said rear panel by an integral hinge.

25. A disposable receptacle as recited in claim 19, further comprising mounting means for securing said receptacle to a support and for biasing said lid into said closed position thereof.

26. A disposable receptacle as recited in claim 26, wherein said mounting means comprises:
(a) a mount securable to the support; and
(b) cooperating means associated with said rear panel for holding said receptacle on said mount.

27. A disposable receptacle is recited in claim 19, further comprising a flap hingedly attached to said mounting means and spring loaded to urge against said lid to bias said lid into said closed position thereof.

28. A disposable receptacle is recited in claim 27, wherein said cooperating means comprises a mounting finger on the exterior of said back wall, and wherein said mount comprises:
(a) a base plate securable to the support;
(b) a lid-biasing flap resiliently mounted at the top of said base plate for urging said lid into said closed position thereof when said receptacle is secured to said mount; and
(c) a locking plate slidably mounted to said base plate for movement between a receiving position in which said mounting finger is free of said locking plate and a retaining position in which said mounting finger is captured by said locking plate to secure said receptacle to said base plate, said locking plate being biased into said retaining position thereof.

29. A disposable receptacle as recited in claim 28, wherein said locking plate is concealed by said receptacle when said receptacle is secured to said mount and said locking plate is moveable from said retaining position to said receiving position to free said mounting finger from said locking plate by a key insertable between said receptacle and said base plate.

30. A system for cleanly storing and disposing of discarded articles, said system comprising:
(a) a rear panel having a back wall for mounting to a support, two side walls projecting from said back wall in a direction opposite the support, and a floor interconnecting said side walls and said back wall, said floor being inclined upwardly from said back wall when said receptacle is mounted on the support to form in combination with said back wall and side walls an open-topped reservoir for trapping fluid from the discarded articles;
(b) a face panel attached to said floor of said rear panel between said side walls by an integral hinge, said face panel being pivotable about said hinge into an opposing relationship with said back wall and a mating relationship with said side walls to form above said reservoir an enclosure accessible through an opening formed between the top of said face panel and the top of said back wall;
(c) fastening means on said face panel and on said sides of said rear panel for retaining said face panel and said back wall in said opposing relationship;
(d) a lid attached to said top of said back wall by an integral lid hinge, said lid being pivotable about said lid hinge to occlude said opening to said enclosure in a closed position of said lid;
(e) a mounting finger on the exterior of said back wall of said rear panel;
(f) a base plate securable to the support;
(g) a lid-biasing flap resiliently mounted at the top of said base plate for urging said lid into said closed position thereof when said receptacle is secured to said mount;
(h) a locking plate slidably mounted to said base plate for movement between a receiving position in which said mounting finger is free of said locking plate and a retaining position in which said mounting finger is captured by said locking plate to secure said receptacle to said base plate, said locking plate being biased into said retaining position thereof; and
(i) a key insertable between said receptacle and said base plate to free said mounting finger from said locking plate by moving said locking plate from the retaining to the receiving position thereof.

31. A disposable receptacle as recited in claim 30, wherein said rear panel with said face panel and with said lid pivotably attached thereto is nestable with other identically configured and identically attached rear and face panels when said face panel and said back wall are out of said opposing relationship.

32. A system for cleanly storing and disposing of discarded articles as recited in claim 30, wherein on the side of said enclosure opposite said reservoir said face and back panels form therebetween a non-linear passageway leading from said enclosure to said opening.

33. A system for cleanly storing and disposing of used articles containing fluid as recited in claim 30, further comprising a guard plate projecting from said lid toward said opening proximate said lid hinge, said guard plate at least partially closing said opening when said lid is pivoted out of said closed position thereof and being housed in the interior of said enclosure when said lid is pivoted into said closed position thereof.

34. A method for cleanly storing and disposing of discarded articles, said method of comprising the steps:
   (a) releasably mounting on a support a disposable receptacle having an enclosure for the articles and therebelow an open-topped reservoir for trapping fluid from the articles;
   (b) depositing discarded articles in the receptacle;
   (c) removing said receptacle with the discarded articles deposited therein from said support; and
   (d) disposing of said receptacle with the discarded articles therein.

35. A method as recited in claim 34, wherein said step of releasably mounting comprises the steps:
   (a) folding a unitary, nestable sequence of interconnected panels into a disposable receptacle having an enclosure for the articles and therebelow an opentopped reservoir for trapping fluid from the articles;
   (b) attaching a mount for said receptacle to the support; and
   (c) releasably securing said receptacle to said mount.

36. A method as recited in claim 35, wherein said unitary, nestable sequence of interconnected panels comprises:
   (a) a rear panel having a back wall for attachment to said mount, two side walls projecting from said back wall, and a floor extending from said back wall at an acute angle interconnecting said side walls to form in combination with said back wall and side walls an opentopped reservoir for trapping fluid from the discarded articles;
   (b) a face panel pivotably attached to said floor between said side walls by an integral hinge, said face panel being pivotable about said hinge into an opposing relationship with said back wall and a mating relationship with said side walls to form about said reservoir an enclosure accessible through an opening formed between the top of said face panel and top of said back wall;
   (c) a lid pivotably attached to said top of said back wall by an integral hinge for occluding said opening to said enclosure in a closed position of said lid; and
   (d) fastening means on said face panel and on said side walls for retaining said face panel and said back wall in said opposing relationship; and
wherein said step of assembling comprises the steps of pivoting said face panel into said opposing relationship with said back wall and engaging said fastening means.

37. A method as recited in claim 35, wherein a mounting finger is provided on the exterior of said receptacle, wherein said mount comprises:
   (a) a base plate;
   (b) a locking plate slidably mountable to said base plate for movement between a receiving position in which said mounting finger is free of said locking plate and a retaining position in which said mounting finger is captured by said locking plate; and
wherein said step of attaching comprises the steps securing said base plate to the support and slidably mounting said locking plate to said base plate.

38. A method as recited in claim 36, wherein said step of depositing comprises the steps:
   (a) pivoting said lid out of said closed position thereof;
   (b) entering a discarded article through said opening into said enclosure; and
   (c) pivoting said lid into said closed position thereof.

39. A method as recited in claim 36, wherein said unitary, nestable sequence of interconnected panels further comprises a guard plate projecting from said lid toward said opening, said guard plate at least partially closing said opening when said lid is pivoted out of said closed position thereof and being housed in the interior of said enclosure when said lid is pivoted into said closed position thereof, and wherein said step of depositing comprises the steps:
   (a) pivoting said lid out of said closed position thereof;
   (b) placing a discarded article on said guard plate; and
   (c) pivoting said lid into said closed position thereof, thereby dumping the discarded article on said guard plate into said enclosure.

40. A method as recited in claim 37, wherein said step of removing comprises inserting a key between said receptacle and said base plate to move said locking plate from the retaining to the receiving position thereof and free said mounting finger from said locking plate.

* * * * *